United States Patent
Froehner et al.

(10) Patent No.: US 9,382,581 B2
(45) Date of Patent: Jul. 5, 2016

(54) PRIMERS WITH MODIFIED PHOSPHATE AND BASE IN ALLELE-SPECIFIC PCR

(71) Applicant: Roche Molecular Systems, Inc., Pleasanton, CA (US)

(72) Inventors: Stefanie Froehner, Penzberg (DE); Dieter Heindl, Paehl (DE); Dirk Kessler, Peiting (DE); Nancy Schoenbrunner, Moraga, CA (US); Alison Tsan, Danville, CA (US)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 226 days.

(21) Appl. No.: 14/092,133

(22) Filed: Nov. 27, 2013

(65) Prior Publication Data

US 2014/0170650 A1    Jun. 19, 2014

Related U.S. Application Data

(60) Provisional application No. 61/736,742, filed on Dec. 13, 2012.

(51) Int. Cl.
*C12Q 1/68* (2006.01)
*C12P 19/34* (2006.01)

(52) U.S. Cl.
CPC ............ *C12Q 1/6853* (2013.01); *C12Q 1/6858* (2013.01)

(58) Field of Classification Search
CPC ........................... C12Q 1/6853; C12Q 1/6858
USPC .................................................. 435/6.1, 91.1
See application file for complete search history.

(56) References Cited

U.S. PATENT DOCUMENTS

| 5,137,806 | A | 8/1992 | LeMaistre et al. |
| 5,639,611 | A | 6/1997 | Wallace et al. |
| 6,001,611 | A | 12/1999 | Will |
| 7,408,051 | B2 | 8/2008 | Ma et al. |
| 7,741,472 | B2 | 6/2010 | Heindl et al. |
| 2010/0099110 | A1 | 4/2010 | Will et al. |
| 2011/0311968 | A1 | 12/2011 | Will et al. |
| 2012/0164641 | A1 | 6/2012 | Bauer et al. |
| 2013/0078630 | A1 | 3/2013 | Bodepudi et al. |

FOREIGN PATENT DOCUMENTS

| EP | 0866071 A2 | 3/1998 |
| EP | 0866071 A3 | 3/1998 |
| EP | 1801114 A1 | 6/2007 |
| WO | 2008128686 A1 | 10/2008 |
| WO | 2010046067 A1 | 4/2010 |
| WO | 2011069677 A1 | 6/2011 |
| WO | PCTEP2013076148 | 4/2014 |

OTHER PUBLICATIONS

Gaster, Jens, et al., 2005, "Tuning Single Nucleotide Discrimination in Polymerase Chain Reactoins (PCRs): Synthesis of Primer Probes Bearing Polar 4'-C-Modifications and Their Application in Allele-Specific PCR," Chemistry European Journal, 11:1861-1870.

*Primary Examiner* — Jezia Riley
(74) *Attorney, Agent, or Firm* — David J Chang

(57) ABSTRACT

The present invention includes a method of allele-specific amplification, utilizing an allele-specific oligonucleotide, at least partially complementary to more than one variant of the target sequence, but having at least one selective nucleotide complementary to only one variant of the target sequence and incorporating both a nucleotide with a base covalently modified at the exocyclic amino group and a modified phosphate.

6 Claims, No Drawings

SEQUENCE LISTING

<160> NUMBER OF SEQ ID NOS: 25

<210> SEQ ID NO 1
<211> LENGTH: 23
<212> TYPE: DNA
<213> ORGANISM: Artificial Sequence -continued

```
<220> FEATURE:
<223> OTHER INFORMATION: Synthetic primer

<400> SEQUENCE: 1
agcctcttac acccagtgga gaa                                           23

<210> SEQ ID NO 2
<211> LENGTH: 33
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' Phosphate
<220> FEATURE:
<221> NAME/KEY: misc_feature
<222> LOCATION: (10)..(11)
<223> OTHER INFORMATION: BHQ-2 dye between bases

<400> SEQUENCE: 2
agctctcttg aggatcttga aggaaactga att                                33

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
ccagaccatg agaggccctg                                               20

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
tgtcgaacgc accggagct                                                19

<210> SEQ ID NO 5
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(18)
<223> OTHER INFORMATION: pABSA modification between bases

<400> SEQUENCE: 5
gtgccgaacg caccggagct                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(18)
```

<223> OTHER INFORMATION: pABSA modification between bases

<400> SEQUENCE: 6
gtgccgaacg caccggagtt                                                      20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (17)..(17)
<223> OTHER INFORMATION: tbbdC
<220> FEATURE:
<221> NAME/KEY: misc_feature
<222> LOCATION: (19)..(20)
<223> OTHER INFORMATION: pABSA modification between bases

<400> SEQUENCE: 7
gtgccgaacg caccggcgct                                                      20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (19)..(20)
<223> OTHER INFORMATION: pABSA modification between bases

<400> SEQUENCE: 8
gtgccgaacg caccggagct                                                      20

<210> SEQ ID NO 9
<211> LENGTH: 25
<212> TYPE: DNA
<213> ORGANISM: Artificial Sequence
<220> FEATURE:
<223> OTHER INFORMATION: Synthetic primer

<400> SEQUENCE: 9
gtcttctctg tttcagggca tgaac                                                25

<210> SEQ ID NO 10
<211> LENGTH: 25
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' phosphate
<220> FEATURE:
<221> NAME/KEY: misc_feature
<222> LOCATION: (10)..(11)
<223> OTHER INFORMATION: BHQ-2 between bases
<220> FEATURE:
<221> NAME/KEY: misc_feature
<222> LOCATION: (10)..(11)
<223> OTHER INFORMATION: BHQ-2 dye between bases

<400> SEQUENCE: 10
tactggtgaa aacaccgcag catgt                                                25

```
<210> SEQ ID NO 11
<211> LENGTH: 22
<212> TYPE: DNA
<213> ORGANISM: Artificial Sequence
<220> FEATURE:
<223> OTHER INFORMATION: Synthetic primer

<400> SEQUENCE: 11
ctggtccctg gtgtcaggaa aa                                           22

<210> SEQ ID NO 12
<211> LENGTH: 19
<212> TYPE: DNA
<213> ORGANISM: Artificial Sequence
<220> FEATURE:
<223> OTHER INFORMATION: Synthetic primer

<400> SEQUENCE: 12
gcgcccagca gtttggccc                                               19

<210> SEQ ID NO 13
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(16)
<223> OTHER INFORMATION: pABSA modification between bases
<220> FEATURE:
<221> NAME/KEY: modified_base
<222> LOCATION: (17)..(17)
<223> OTHER INFORMATION: N4-ethyl-dC

<400> SEQUENCE: 13
gcacccagca gtttggcac                                               19

<210> SEQ ID NO 14
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: modified_base
<222> LOCATION: (17)..(17)
<223> OTHER INFORMATION: N4-ethyl-dC
<220> FEATURE:
<221> NAME/KEY: misc_feature
<222> LOCATION: (18)..(19)
<223> OTHER INFORMATION: pABSA modification between bases

<400> SEQUENCE: 14
gcacccagca gtttggac                                                18

<210> SEQ ID NO 15
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(17)
<223> OTHER INFORMATION: pABSA modification between bases

<400> SEQUENCE: 15
```

```
gcacccagca gtttggccc                                              19

<210> SEQ ID NO 16
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (17)..(18)
<223> OTHER INFORMATION: pABSA modification between bases

<400> SEQUENCE: 16
gcacccagca gtttggccc                                              19

<210> SEQ ID NO 17
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(19)
<223> OTHER INFORMATION: pABSA modification between bases

<400> SEQUENCE: 17
gcacccagca gtttggccc                                              19

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18
cctccctcca ggaagcctac gtga                                        24

<210> SEQ ID NO 19
<211> LENGTH: 21
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: 5' JA-270
<220> FEATURE:
<221> NAME/KEY: misc_feature
<223> OTHER INFORMATION: 3' phosphate
<220> FEATURE:
<221> NAME/KEY: misc_feature
<222> LOCATION: (14)..(15)
<223> OTHER INFORMATION: BHQ-2 dye between bases

<400> SEQUENCE: 19
tgcacggtgg aggtgaggca g                                           21

<210> SEQ ID NO 20
<211> LENGTH: 23
<212> TYPE: DNA
```

```
<213> ORGANISM: Artificial Sequence
<220> FEATURE:
<223> OTHER INFORMATION: Synthetic primer

<400> SEQUENCE: 20
tgcgatctgc acacaccagt tga                                              23

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
cagtcgaagg gcatgagctg ca                                               22

<210> SEQ ID NO 22
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(19)
<223> OTHER INFORMATION: pABSA modification between bases
<220> FEATURE:
<221> NAME/KEY: modified_base
<222> LOCATION: (21)..(21)
<223> OTHER INFORMATION: tbbdC

<400> SEQUENCE: 22
cagccgaagg gcatgagctg ca                                               22

<210> SEQ ID NO 23
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (18)..(19)
<223> OTHER INFORMATION: pABSA modification between bases

<400> SEQUENCE: 23
cagccgaagg gcatgagctg ca                                               22

<210> SEQ ID NO 24
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(22)
<223> OTHER INFORMATION: pABSA modification between bases

<400> SEQUENCE: 24
cagccgaagg gcatgagctg ca                                               22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer
```

```
<220> FEATURE:
<221> NAME/KEY: misc_feature
<222> LOCATION: (21)..(22)
<223> OTHER INFORMATION: pABSA modification between bases

<400> SEQUENCE: 25
cagccgaagg gcatgagcgg ca                                          22
```

PRIMERS WITH MODIFIED PHOSPHATE AND BASE IN ALLELE-SPECIFIC PCR

CROSS REFERENCE TO RELATED INVENTION

This application claims the benefit of priority of U.S. Provisional Patent Application Ser. No. 61/736,742, filed Dec. 13, 2012, which is incorporated herein by reference in its entirety.

REFERENCE TO SEQUENCE LISTING

This application contains a Sequence Listing submitted as an electronic text file named "31353_US1.txt", having a size in bytes of 8 kb, and created on Oct. 25, 2013. The information contained in this electronic file is hereby incorporated by reference in its entirety pursuant to 37 CFR §1.52(e)(5).

FIELD OF THE INVENTION

The invention relates to the field of nucleic acid amplification and specifically, to the field of allele-specific amplification.

BACKGROUND OF THE INVENTION

Allele-specific amplification of nucleic acids allows for simultaneous amplification and analysis of the target sequence. Allele-specific amplification is commonly used when the target nucleic acid is suspected of having one or more subpopulations with a variation (polymorphism) in its sequence. DNA polymorphisms are used in DNA profile analysis (forensics, paternity testing, tissue typing for organ transplants), genetic mapping, as well as detection of rare mutations, such as those occurring in cancer cells in the background of cells with normal DNA.

In a successful allele-specific amplification, the desired variant of the target nucleic acid is amplified, while the other variants are not, at least not to a detectable level. A typical allele-specific amplification assay involves a polymerase chain reaction (PCR) where at least one primer is complementary to the region with a suspected polymorphism. The design of the allele-specific primer is such that primer extension occurs only when a certain variant of the polymorphism is present. In its simplest form, the allele-specific primer has a 3'-terminal nucleotide complementary to the desired variant of the polymorphic nucleotide in the target. Often a single mismatch at the 3'-terminus of the primer is sufficient to preclude amplification of the undesired variants of the target sequence. However, specificity of amplification varies greatly among different 3'-terminal sequences: some mismatches effectively block extension by the polymerase, while others do not, see U.S. Pat. No. 5,639,611.

The success of allelic discrimination depends on the inability of the DNA polymerase to extend mismatched primers. This inability of the DNA polymerase may be modulated by adjusting the reaction conditions to achieve maximum selectivity. Nevertheless, poor selectivity of allele-specific PCR remains a problem for many polymorphic sequences.

One approach to increasing specificity involves engineering amplification primers with an internal mismatched nucleotide or nucleotides. This approach proved successful in some systems, see U.S. Pat. No. 5,137,806.

Another approach to increasing specificity involves chemical modification of the primers. For example, it was found that certain 2'-C and 4'-C modifications of the deoxyribose of some nucleotides in the primer enhance allele discrimination by the polymerase. See Gaster, J. and Marx, A., Chem. Eur. J. 2005, 11:1861-1870. In another study, it was found that allelic discrimination is enhanced by the use of an unnatural pyrimidine base in one of the nucleotides in the primer, specifically, pseudoisocytidine with various substituents in the 6-position of the pyrimidine ring, see U.S. Pat. No. 7,408,051.

In the context of real-time allele-specific PCR, the selectivity of the assay may be measured as the difference in the threshold cycle number (Ct) between the matched and mismatched templates. A greater difference indicates a greater delay in amplification of the mismatched template and thus a greater discrimination between alleles. The modified deoxyribose has been shown to result in Ct differences of between 1 and 14 cycles. The use of pseudoisocytidine resulted in a 7-cycle delay in amplification of the mismatched template. This degree of discrimination is insufficient for many applications, where the sample contains several variants of the template, all competing for amplification. Often the mismatched template is present in much greater amounts than the matched template. For example, in tissue samples, only a small fraction of cells may be malignant and carry the mutation ("matched template"), targeted by the allele-specific amplification assay. The template present in normal cells may be amplified less efficiently, but the overwhelming numbers of normal cells will overcome any delay in amplification and erase any advantage of the mutant template. To detect rare mutations in the presence of the wild-type template, the specificity of the allele-specific amplification assay needs to be improved.

Many ways of enhancing allele-specificity of primers have been proposed. However, for many clinically-relevant nucleic acid targets, the lack of specificity of PCR remains a problem. Therefore, novel approaches to the design of allele-specific primers are necessary.

Nucleotides and oligonucleotides containing modified phosphate residues have been described in U.S. Pat. No. 7,741,472. The key feature of this modified phosphate was to start with a trivalent phosphorus atom and to react it with a reagent in such a manner that a stable phosphate mimetic is formed. A phosphorus atom containing at least one hydroxyl residue which was provided with a protective group was reacted with an azide having the structure N=N=N-Acc in which Acc is an electron acceptor or an electron acceptor substituted with a residue R and R is any organic substituent. This results in the formation of a pentavalent phosphorus atom to which a strongly electron-attracting electron acceptor group is covalently bound via an N atom. This group ensures that the oligonucleotides produced in this manner are, in contrast to the phosphoramidate compounds, resonance-stabilized and are not susceptible to hydrolysis.

SUMMARY OF THE INVENTION

In a first aspect, the invention relates to a method of allele-specific amplification of a variant of a target sequence, the target existing in the form of several variant sequences, the method comprising, (a) hybridizing a first oligonucleotide and a second oligonucleotide to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

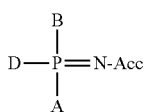

wherein A and B represents a nucleotide chain, D is OH or CH$_3$, and Acc is an electron acceptor or an electron acceptor substituted with a residue R wherein R is an organic substituent, wherein Acc is selected from the group consisting of CN, SO$_2$—R', in which R' comprises at least one amino-substituted alkyl, an optionally substituted aryl or an optionally substituted heterocycle, and a six membered N$^+$ heterocycle with at least one alkylated N-atom in ortho- or para-position, said heterocycle selected from the group consisting of pyridinium, pyrimidinium, and quinolinium; (b) providing conditions suitable for oligonucleotide extension by a nucleic acid polymerase; (c) extending said first oligonucleotide and said second oligonucleotide by said nucleic acid polymerase, wherein said nucleic acid polymerase is capable of extending said second oligonucleotide efficiently when said oligonucleotide is hybridized to a variant of the target sequence which is complementary to said at least one selective nucleotide, and substantially less efficiently when said second oligonucleotide is hybridized to a variant of the target sequence which is not complementary to said at least one selective nucleotide.

In a second aspect, the invention relates to a method of detecting a variant of a target sequence, the target existing in the form of several variant sequences, the method comprising, (a) hybridizing a first oligonucleotide and a second oligonucleotide to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

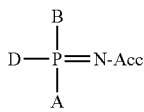

wherein A and B represents a nucleotide chain, D is OH or CH$_3$, and Acc is an electron acceptor or an electron acceptor substituted with a residue R wherein R is an organic substituent, wherein Acc is selected from the group consisting of CN, SO$_2$—R', in which R' comprises at least one amino-substituted alkyl, an optionally substituted aryl or an optionally substituted heterocycle, and a six membered N$^+$ heterocycle with at least one alkylated N-atom in ortho- or para-position, said heterocycle selected from the group consisting of pyridinium, pyrimidinium, and quinolinium; (b) providing conditions suitable for oligonucleotide extension by a nucleic acid polymerase; (c) extending said first oligonucleotide and said second oligonucleotide by said nucleic acid polymerase, wherein said nucleic acid polymerase is capable of extending said second oligonucleotide efficiently when said oligonucleotide is hybridized to a variant of the target sequence which is complementary to said at least one selective nucleotide, and substantially less efficiently when said second oligonucleotide is hybridized to a variant of the target sequence which is not complementary to said at least one selective nucleotide; (d) detecting products of said oligonucleotide extension, wherein said extension signifies the presence of the variant of said target sequence to which said second oligonucleotide has a complementary selective nucleotide.

In a third aspect, the invention relates to a kit for allele-specific amplification of a target sequence, the target existing in the form of several variant sequences, the kit comprising, (a) a first oligonucleotide, at least partially complementary to one or more variant of the target sequence; and (b) a second oligonucleotide, at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

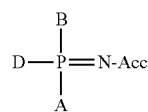

wherein A and B represents a nucleotide chain, D is OH or CH$_3$, and Acc is an electron acceptor or an electron acceptor substituted with a residue R wherein R is an organic substituent, wherein Acc is selected from the group consisting of CN, SO$_2$—R', in which R' comprises at least one amino-substituted alkyl, an optionally substituted aryl or an optionally substituted heterocycle, and a six membered N$^+$ heterocycle with at least one alkylated N-atom in ortho- or para-position, said heterocycle selected from the group consisting of pyridinium, pyrimidinium, and quinolinium.

In a fourth aspect, the invention relates to an oligonucleotide for performing an allele-specific amplification of a target sequence, the target existing in the form of several variant sequences, the oligonucleotide comprising, (a) a sequence at least partially complementary to a portion of one or more variants of said target sequence; (b) at least one selective nucleotide complementary to only one variant of the target sequence; (c) a nucleotide with a base covalently modified at the exocyclic amino group; (d) a modified phosphate having a structure:

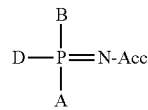

wherein A and B represents a nucleotide chain, D is OH or CH$_3$, and Acc is an electron acceptor or an electron acceptor substituted with a residue R wherein R is an organic substituent, wherein Acc is selected from the group consisting of CN, SO$_2$—R', in which R' comprises at least one amino-substituted alkyl, an optionally substituted aryl or an optionally substituted heterocycle, and a six membered N$^+$ heterocycle with at least one alkylated N-atom in ortho- or para-position, said heterocycle selected from the group consisting of pyridinium, pyrimidinium, and quinolinium.

In a fifth aspect, the invention relates to a reaction mixture for allele-specific amplification of a target sequence, the target existing in the form of several variant sequences, the mixture comprising, (a) a first oligonucleotide, at least partially complementary to one or more variant of the target sequence; and (b) a second oligonucleotide, at least partially complementary to one or more variants of the target sequence, and has at least one selective nucleotide complementary to only one variant of the target sequence; wherein said second oligonucleotide comprises both a nucleotide with a base covalently modified at the exocyclic amino group and a modified phosphate having a structure:

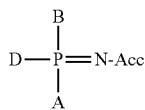

wherein A and B represents a nucleotide chain, D is OH or CH$_3$, and Acc is an electron acceptor or an electron acceptor substituted with a residue R wherein R is an organic substituent, wherein Acc is selected from the group consisting of CN, SO$_2$—R', in which R' comprises at least one amino-substituted alkyl, an optionally substituted aryl or an optionally substituted heterocycle, and a six membered N$^+$ heterocycle with at least one alkylated N-atom in ortho- or para-position, said heterocycle selected from the group consisting of pyridinium, pyrimidinium, and quinolinium; (c) a nucleic acid polymerase; (d) nucleoside triphosphates; and (e) a buffer suitable for the extension of nucleic acids by the nucleic acid polymerase.

DETAILED DESCRIPTION OF THE INVENTION

Definitions

Unless defined otherwise, all technical and scientific terms used herein have the same meaning as commonly understood by one of ordinary skill in the art to which this invention pertains. In describing and claiming the present invention, the following definitions will be used.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphosphoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Helv. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

A "purine nucleotide" refers to a nucleotide that comprises a purine base, whereas a "pyrimidine nucleotide" refers to a nucleotide that comprises a pyrimidine base.

An "oligonucleotide" refers to a nucleic acid polymer that includes at least two, but typically 5-50 nucleotides and more typically, between 15 and 35 nucleotides. The exact size of an oligonucleotide generally depends on various factors, including the ultimate function or use of the oligonucleotide. Oligonucleotides may be prepared by any suitable method known in the art, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103: 3185-3191; automated synthesis methods; the solid support method of U.S. Pat. No. 4,458,066 or any other chemical method known in the art.

A "primer nucleic acid" or "primer" is an oligonucleotide that can hybridize to a template nucleic acid and permit chain extension or elongation using a nucleotide incorporating biocatalyst. Although other primer lengths are sometimes utilized, primers typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. However, the success of the extension generally requires greater complementarity (i.e. fewer mismatches with the template) at the 3'-end of the primer. A primer nucleic acid can be labeled, if desired, by incorporating a label detectable by radiological, spectroscopic, photochemical, biochemical, immunochemical, or chemical techniques.

An "extended primer" refers to a primer to which one or more additional nucleotides have been added. "Primer extension" is the action of the enzyme by which additional nucleotides are added to the primer.

A "template nucleic acid", "template" or "target" refers to a nucleic acid to which a primer nucleic acid can hybridize and be extended under suitable conditions. In the context of nucleic acid amplification, "target" is preferably a region of double stranded nucleic acid, consisting of the sequences at least partially complementary to at least two primer sequences and the intervening sequence. A target can also be a single stranded nucleic acid, consisting of a sequence at least partially complementary to one primer and a sequence partially identical to the second primer. Template nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, tissues, sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

As used herein, a "gene" refers to any segment of DNA associated with a biological function. Thus, genes include coding sequences and optionally, the regulatory sequences required for the expression of the coding sequences.

Nucleic acids are "extended" or "elongated" when additional nucleotides are incorporated into the nucleic acids, for example by a nucleotide incorporating biocatalyst, at the 3' end of a nucleic acid.

A "moiety" or "group" refers to one of the portions into which something, such as a molecule, is divided (e.g., a functional group, substituent group, or the like). For example, a nucleotide typically comprises a base group (e.g., adenine, thymine, cytosine, guanine, uracil, or an analog), a sugar moiety, and one or more phosphate groups.

An "alkyl group" refers to a linear, branched, or cyclic saturated hydrocarbon moiety and includes all positional isomers, e.g., methyl, ethyl, propyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkoxy group" refers to an alkyl group that comprises an oxygen atom and includes, e.g., methoxy, ethoxy, propoxy, butoxy, pentoxy, heptyloxy, octyloxy, and the like.

An "aryl group" refers to a substituent group of atoms or moiety that is derived from an aromatic compound. Exemplary aryl groups include, e.g., phenyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

An "alkyl-aryl group" refers to a group that comprises alkyl and aryl moieties. Examples of the alkyl-aryl groups include benzyl groups, tolyl groups and xylyl groups.

An "allele-specific primer" is a primer that can hybridize to several variants of the template nucleic acid, but permit elongation by the polymerase when hybridized with only some of the variants of the template nucleic acid. With other variants of the template nucleic acid the primer-template hybrid may not be extended or is extended less efficiently by the polymerase.

Nucleic acids are "extended" or "elongated" when additional nucleotides are incorporated into the nucleic acids, for example by a nucleotide incorporating biocatalyst, at the 3' end of a nucleic acid.

An amplification assay is "selective" or "allele-selective" if it yields predominance (i.e., a majority but less than 100%) of one product over other possible products. An assay is described as "allele-selective" as long as amplification of the undesired (mismatched) variant of the target sequence is detectable. The term "specific" or "allele-specific" with respect to amplification assay is used if one of the possible products is formed exclusively. An assay where amplification of the undesired target is undetectable is called "allele-specific." However, it is understood that as the methods of detection become more sensitive, some assays previously known to be allele-specific, turn out to be allele-selective, i.e. some amplification of undesired variants of the target becomes detectable. Therefore, in the context of this invention, the term "allele-specific" is meant to encompass both strictly allele-specific, as well as allele-selective amplification.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, Thermotoga maritima polymerases, such as TMA-25 and TMA-30 polymerases, Tth DNA polymerase, and the like.

A "modified" enzyme refers to an enzyme comprising an amino acid polymer in which at least one monomer differs from the reference sequence, such as a native or wild-type form of the enzyme or another modified form of the enzyme. Exemplary modifications include monomer insertions, deletions, and substitutions. Modified enzymes also include chimeric enzymes that have identifiable component sequences (e.g., structural or functional domains, etc.) derived from two or more parents. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

A polymerase that "substantially lacks 5'-3' nuclease activity" refers to a polymerase that has 50% or less (e.g., <25%, <20%, <15%, <10%) 5'-3' nuclease activity than Taq DNA polymerase. Methods of measuring 5'-3' nuclease activity and conditions for measurement are well known in the art. See, e.g., U.S. Pat. No. 5,466,591. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

The term "3' to 5' nuclease activity" or "3'-5' nuclease activity" or "proof-reading activity" refers to an activity of a nucleic acid polymerase, whereby nucleotides are removed from the 3' end of the nucleic acid strand. For example, *E. coli* DNA polymerase III has this activity, whereas the *Thermus aquaticus* (Taq) DNA polymerase does not.

A "fidelity" or "replication fidelity" is the ability of a nucleic acid polymerase to incorporate a correct nucleotide during template-dependent polymerization. In the context of replication fidelity, "correct nucleotide" on the nascent nucleotide strand is the nucleotide paired with the template nucleotide via Watson-Crick base pairing. Replication fidelity of a particular polymerase results from a combination of incorporating correct nucleotides and removing incorrect nucleotides from the 3'-terminus of the nascent nucleotide strand via the 3'-5' nuclease activity of the polymerase. Various methods of measuring fidelity of a nucleotide polymerase are reviewed in Tindall et al. (1988) Fidelity of DNA synthesis by the *Thermus aquaticus* DNA polymerase. Biochemistry, 27:6008-6013. Typically, polymerases with 3'-5' nuclease (proofreading) capability have higher fidelity than polymerases without the proof-reading activity.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, mass-modifying groups, antibodies, antigens, biotin, haptens, and enzymes (including peroxidase, phosphatase, etc.).

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

A "Watson-Crick base pairing" or simply "base pairing" refers to "conventional" hydrogen bonding within a double-stranded nucleic acid molecule. Watson-Crick base pairing is hyrdrogen bonding between adenine and thymine, between guanine and cytosine, between adenine and uracil, and between analogs of these bases.

A "selective nucleotide" is a nucleotide in an allele-specific primer that confers allele selectivity to the primer. The selective nucleotide is complementary to a corresponding nucleotide in the desired variant of the target nucleic acids but not complementary to the corresponding nucleotide in the undesired variants of the target nucleic acid. In a primer, more than one nucleotide may be complementary to a nucleotide in the desired variants of the target nucleic acids but not complementary to the corresponding nucleotide in the undesired variants of the target nucleic acid. However, the selective nucleotide is located at a position within the primer that affects the specificity of the primer. The selective nucleotide permits efficient or inefficient amplification of the target nucleic acid, depending on whether or not it finds or does not find a complementary partner in the target nucleic acid. A primer may contain more than one selective nucleotide.

The expression "wherein said polymerase is capable of extending said second oligonucleotide efficiently when said second oligonucleotide is hybridized to a variant of the target sequence which is complementary to the at least one selective nucleotide, and substantially less efficiently when said second oligonucleotide is hybridized to a variant of the target sequence which is not complementary to the at least one selective nucleotide." means that extension of the second oligonucleotide by the polymerase is more efficient when the selective nucleotide forms a base pair with the target, than when said selective nucleotide does not form a base pair with the target.

As mentioned above, in one aspect, the present invention relates to a method of allele-specific amplification, comprising (a) providing a sample, possibly containing at least one variant of a target sequence; (b) providing a first oligonucleotide, at least partially complementary to more than one variant of the target sequence; (c) providing a second oligonucleotide, at least partially complementary to one or more variants of the target sequence, having a selective nucleotide complementary to only one variant of the target sequence; wherein said second oligonucleotide comprises both a nucleotide with a base covalently modified at the exocyclic amino group and a modified phosphate; (d) providing conditions suitable for the hybridization of said first and second oligonucleotides to at least one variant of the target sequence; (e) providing conditions suitable for the oligonucleotide extension by a nucleic acid polymerase; wherein said polymerase is capable of extending said second oligonucleotide when it is hybridized to the variant of the target sequence for which it has said complementary selective nucleotide, and substantially less when said second oligonucleotide is hybridized to the variant of the target sequence for which it has a non-complementary selective nucleotide.

The second oligonucleotide, at least partially complementary to one or more variants of the target sequence, having a selective nucleotide complementary to only one variant of the target sequence is referred to as a "selective oligonucleotide," "selective primer," or "allele-selective primer." The selective oligonucleotide of the present invention comprises 10-50, more preferably 15-35 nucleotides, the majority of them complementary to a sequence in more than one variant of the target sequence. The selective nucleotide of the oligonucleotide is complementary to a variant of the target sequence that is to be amplified and not complementary to other variants. In one embodiment, the selective nucleotide is the 3'-terminal nucleotide. The selective oligonucleotide of the present invention includes one or more nucleotides with a base, covalently modified at the exocyclic amino group. In some embodiments, the modified-base nucleotide occurs between 1 and 5 nucleotides upstream of the 3'-terminal nucleotide (also designated as -1, -2, -3, -4, -5 or N-1, N-2, N-3, N-4, N-5 positions herein). In other embodiments, the modified-base nucleotide is the 3'-terminal nucleotide. In some embodiments, the modified-base nucleotide occurs both at the 3'-terminus and at least once more, elsewhere within the oligonucleotide.

The nucleotides with covalent modifications of the exocyclic amino groups have been described in U.S. Pat. No. 6,001,611, ('611) which is incorporated herein by reference in its entirety. The synthesis of such nucleotides, and oligonucleotides incorporating such nucleotides are also described in the '611 patent.

The examples of exocyclic amino groups include the amino groups in the 6-position of adenosine, 2-position of guanosine and 4-position of cytidine. Exocyclic amino groups that take part in base pairing with the complementary nucleic acid strand may also occur in various unconventional nitrogenous bases in nucleotides. Examples of nucleosides with unconventional bases include, without limitation, 3-methyladenosine, 7-methylguanosine, 3-methylguanosine, 5-methylcytidine, and 5-hydroxymethylcytidine. Suitable modifications of exocyclic amino groups of such unconventional bases may also be selected according to the empirical method of the present invention.

The structures of the modified nucleotides containing a modified adenine, guanine, and cytosine base, respectively, are shown below,

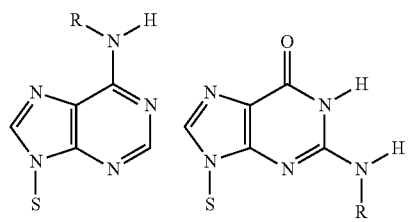

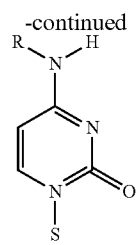

where S represents the sugar moiety, and R represents the modifier group. A variety of modifier groups are envisioned which possess the four properties outlined above. In certain embodiments, modifier groups have the structure:

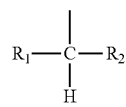

wherein $R_1$ and $R_2$ are independently selected from the group consisting of hydrogen, alkyl, alkoxy, unsubstituted or substituted aryl and phenoxy.

Alkyl groups may be branched or unbranched

Alkyl groups can be $C_1$-$C_{20}$ alkyls, for example $C_1$-$C_{10}$ alkyls.

Alkoxy groups can be $C_1$-$C_{20}$ alkoxy, for example $C_1$-$C_{10}$ alkoxy.

Aryl can be unsubstituted or substituted phenyl or naphtyl.

In one embodiment, R is a benzyl group or a substituted benzyl group. In certain embodiments, substituted benzyl groups can have the following structure:

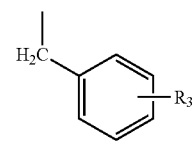

wherein $R_3$ represents a $C_1$-$C_6$ branched or unbranched alkyl group, more preferably a $C_1$-$C_4$ branched or unbranched alkyl group, an alkoxy group, or a nitro group. Preferably, $R_3$ is attached in the para-position.

In some embodiments, the modifier groups are represented by structures shown below:

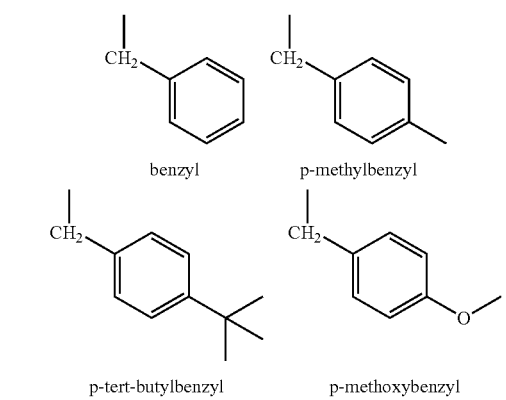

benzyl     p-methylbenzyl p-tert-butylbenzyl     p-methoxybenzyl

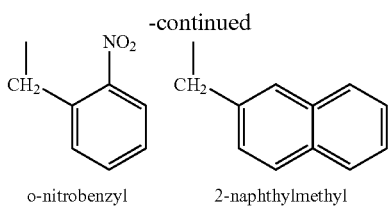

o-nitrobenzyl        2-naphthylmethyl

In general, empirical selection of a particular suitable modifier group from the class of compounds described herein can be carried out routinely by one of skill in the art, based on the presence of the four properties listed above. Preferably, suitability of a particular group is determined empirically by using the primers with modified nucleotides in an allele-specific amplification reaction. The suitability of the modification is indicated by the increased selectivity of the reaction utilizing a primer with the base modification, when compared to an identical reaction with an unmodified primer.

Synthesis and use of modified phosphate residues have been described in U.S. Pat. No. 7,741,472 ('472), which is incorporated herein by reference in its entirety. A phosphorus atom containing at least one hydroxyl residue is reacted with an azide having the structure N=N—N-Acc, in which Acc is an electron acceptor or an electron acceptor substituted with a residue R and R is any organic substituent. On example of a modified phosphate has the structure:

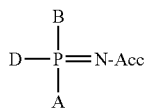

in which, A and B represents a nucleotide chain, D is OH or $CH_3$, and Acc is selected from the group consisting of CN, $SO_2$—R', in which R' comprises at least one amino-substituted alkyl, an optionally substituted aryl or an optionally substituted heterocycle, and a six membered $N^+$ heterocycle with at least one alkylated N-atom in ortho- or para-position, said heterocycle selected from the group consisting of pyridinium, pyrimidinium, and quinolinium.

Oligonucleotides that contain such modified phosphate residues can be used to hybridize with natural DNA and RNA and function as probes or primers in amplification reactions such as real-time PCR. One embodiment of a modified phosphate has the structure:

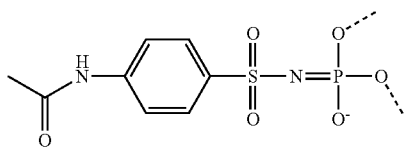

and is referred in the '472 patent as P(=NSO2PhNHAc) or pABSA. Other embodiments of modified phosphates described in the '472 patent include P=pPh-NAc, P(=N—$SO_2$-Ph-p-N=N-Ph-p-$NMe_2$), and P=NS(O)2-rhodamine-B. Real-time PCR and melting curve analysis on the use of oligonucleotide primers that incorporate these modified phosphates have also been described in the '472 patent.

The allele-specific primer of the present invention may incorporate various aspects of primer design known in the art. For example, the primer may take the form of a unimolecular primer-probe combination termed "scorpion" and described in Whitcombe et al., (1999) Detection of PCR products using self-probing amplicons and fluorescence, Nature Biotech. 17:804-807. The scorpion primer designed according to the present invention incorporates the typical elements of the scorpion, namely a probe portion, a stem loop portion and a primer portion. Further, in a scorpion designed according to the present invention, the primer portion has a 3' end complementary to the variant position. The primer portion in a scorpion designed according to the present invention contains one or more modified-base nucleotides and one or more modified phosphates as described herein.

In some embodiments of the invention, the amplification involves the polymerase chain reaction, i.e. repeated cycles of template denaturation, annealing (hybridization) of the oligonucleotide primer to the template, and extension of the primer by the nucleic acid polymerase. In some embodiments, the annealing and extension occur at the same temperature step.

In some embodiments, the amplification reaction involves a hot start protocol. In the context of allele-specific amplification, the selectivity of the allele-specific primers with respect to the mismatched target may be enhanced by the use of a hot start protocol. Many hot start protocols are known in the art, for example, the use of wax, separating the critical reagents from the rest of the reaction mixture (U.S. Pat. No. 5,411,876), the use of a nucleic acid polymerase, reversibly inactivated by an antibody (U.S. Pat. No. 5,338,671), a nucleic acid polymerase reversibly inactivated by an oligonucleotide that is designed to specifically bind its active site (U.S. Pat. No. 5,840,867) or the use of a nucleic acid polymerase with reversible chemical modifications, as described e.g. in U.S. Pat. Nos. 5,677,152 and 5,773,528.

In some embodiments of the invention, the allele-specific amplification assay is the real-time PCR assay. In a real-time PCR assay, the measure of amplification is the "cycles to threshold" or Ct value. An earlier Ct value reflect the rapid achievement of the threshold level and thus a more efficient amplification. The later Ct value may reflect inefficient or inhibited amplification. In the context of an allele-specific real-time PCR assay, the difference in Ct values between the matched and the mismatched templates is a measure of the discrimination between the alleles or the selectivity of the assay.

The allele-specific amplification assay may employ any suitable nucleic acid polymerase known in the art. For an allele-specific PCR assay, any thermostable nucleic acid polymerase may be used. It is sometimes desirable to use an enzyme without the proof-reading (3'-5'-exonuclease) activity, such as for example, Taq DNA polymerase. It may also be desirable to use enzymes, substantially or entirely lacking the 5'-3' nuclease activity, such as described in U.S. Pat. No. 5,795,762. One example of such an enzyme is ΔZ05 polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase.

Detection of the amplification products may be accomplished by any method known in the art. These methods include the use of labeled primers and probes as well as various nucleic acid-binding dyes. The means of detection may be specific to one variant of the target sequence, or may be generic to all variants of the target sequence or even to all double stranded DNA. The non-specific detection methods may be used where the amplification of the undesired variants of the target is minimal and expected to fall below the detection limit of the method.

The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of being the extension products of a labeled primer. After, or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, or at least in the same unopened tube, and no post-amplification handling is required. A homogeneous amplification assay has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probes labeled with two interacting fluorophores, such as "molecular beacon" probes (Tyagi et al., (1996) Nat. Biotechnol., 14:303-308) or fluorescently labeled nuclease probes (Livak et al., (1995) PCR Meth. Appl., 4:357-362). In certain variations of these technologies, an amplification product may also be identified by virtue of its distinctive melting temperature, see U.S. Pat. Nos. 5,871,908 and 6,569,627. The amplification products may also be detected using a unimolecular primer-probe combination termed "scorpion." Whitcombe et al., (1999) Detection of PCR products using self-probing amplicons and fluorescence, *Nature Biotech.* 17:804-807. The primer portion of the scorpion oligonucleotide may be an allele-specific primer designed according to the present invention.

In another aspect, the invention provides a reaction mixture for specifically or selectively amplifying a selected variant of the target sequence, comprising a first oligonucleotide, at least partially complementary to more than one variant of the target sequence, a second oligonucleotide, at least partially complementary to more than one variant of the target sequence, but having a selective nucleotide complementary to only one variant of the target sequence, wherein said second oligonucleotide includes both at least one nucleotide with a base covalently modified at the exocyclic amino group and at least one modified phosphate and also a target nucleic acid, known to exist in more than one sequence variant. In some embodiments, the reaction mixture further comprises the reagents and solutions generally necessary for the amplification of nucleic acids, including a nucleic acid polymerase, nucleic acid precursors, i.e. nucleoside triphosphates, and organic and inorganic ions, suitable for the support of the activity of the nucleic acid polymerase.

In another aspect, the invention provides kits for conducting allele-specific amplification according to the invention. The kit generally includes assay-specific components as well as components generally required for performing DNA amplification assays. As the assay-specific components, the allele-specific amplification kit of the present invention typically includes a first oligonucleotide, at least partially complementary to one or more variant of the target sequence and a second oligonucleotide, at least partially complementary to more than one variant of the target sequence, having a selective nucleotide complementary to only one variant of the target sequence and also having both at least one nucleotide with a base covalently modified at the exocyclic amino group and at least one modified phosphate, and optionally a control nucleic acid sequence comprising an amount of at least one variant of the control target sequence, at least partially complementary to the oligonucleotides enclosed in the kit. In some embodiments, more than one variant of the control nucleic acid sequence may be enclosed. In certain embodiments, among the several variants of the control nucleic acid sequence enclosed in the kit, at least one variant is complementary to the selective nucleotide of the allele-selective oligonucleotide. As the components generally required for nucleic acid amplification, the kit of the present invention typically includes one or more of a nucleic acid polymerase, nucleic acid precursors, such as nucleoside triphosphates (deoxyribonucleoside triphosphates or ribonucleoside triphosphates), optionally, a pyrophosphatase, for minimizing pyrophosphorolysis of nucleic acids, a uracil N-glycosylase (UNG) for protection against carry-over contamination of amplification reactions, pre-made reagents and buffers necessary for the amplification reaction and detection, and a set of instructions for conducting allele-specific amplification of the present invention.

In yet another aspect, the invention provides an oligonucleotide for use in allele-specific PCR. A typical oligonucleotide for use in allele-specific PCR of the present invention comprises 10-50, more preferably 15-35 nucleotides, the majority of them complementary to a sequence in more than one variant of the target sequence. However, the selective nucleotide of the oligonucleotide is complementary to one variant of the target sequence and not complementary to other variants. Further, the oligonucleotide of the present invention includes both at least one nucleotide with a base covalently modified at the exocyclic amino group and a modified phosphate. In some embodiments, the modified-base nucleotide occurs at the 3'-terminal nucleotide. In other embodiments, the modified-base nucleotide occurs between 1 and 5, or for example 1, 2 or 3 nucleotides upstream of the 3'-terminal nucleotide In some embodiments, the modified-base nucleotide occurs both at the 3'-terminus as well as elsewhere within the oligonucleotide.

The following examples and figures are provided to aid the understanding of the present invention, the true scope of which is set forth in the appended claims. It is understood that modifications can be made in the procedures set forth without departing from the spirit of the invention.

EXAMPLES

Example 1

Primers for Detecting Mutation G719S in the Human EGFR Gene

The amplification reactions shown below were carried out using a detection probe (SEQ ID NO: 2) and forward primer (SEQ ID NO:1) common to both wild type and mutant targets. The reverse primer in each reaction is shown in Table 1 as: SEQ ID NO:3, a primer common to both mutant and wild type target; or SEQ ID NO:4, 5, 6, 7, 8, primers that are matched to the G719S mutant target sequence and mismatched to the wild type target at the 3' terminal base position.

Targets used in these reactions are either pooled human WT genomic DNA (provided by Clontech) or a mutant plasmid construct containing a 500 bp G719S sequence insert into a pUC19 plasmid vector (provided by IDT as a minigene).

Mutant or wild type DNA was amplified in reactions that consisted of 50 mM Tris-HCl (pH 8.0), 80 mM potassium Chloride, 160 μM dATP, 160 μM dCTP, 160 μM dGTP, 320 μM dUTP, 0.1 μM each of selective and common primer, 0.05 μM probe, 200 nM NTQ21-46A aptamer, 40 nM Z05-D Mutant polymerase, 10 units of Z05, and 0.1 mM EDTA, 1.25% DMSO, 2.11% Glycerol, and 2.5 mM magnesium acetate. Mutant or wild type targets were present at starting concentrations of approximately 40,000 copies per reaction.

Amplification and analysis were done using the LightCycler 480 instrument. Reactions were thermal cycled using the following profile: Initial 5 min hold at 50 C followed by 2 cycles of cycles of 95° C. (10-seconds) to 62° C. (30-seconds) and 80 cycles of 93 (10-seconds) to 62 (30-seconds). Fluorescence data was collected at the start of each 62° C. anneal step during the 80 cycle PCR.

It was demonstrated that the pABSA modified primers, SEQ ID NO: 5, 6, 7, 8, are more discriminating than the non-pABSA modified primer (SEQ ID NO: 4). Furthermore, the primer containing both N⁴-para-tert-butyl-benzyl cytosine (tbbdC) and pABSA, SEQ ID NO: 7, showed the greatest discrimination. Discrimination is measured as a function of delta Ct between amplification of mutant versus wild type target of equal input (40,000 c). A greater delta Ct is interpreted as greater discrimination of amplification between mutant and wild type alleles.

TABLE 1

| SEQ ID NO: | Sequence | MUT Ct | WT Ct | Delta Ct |
|---|---|---|---|---|
| 1 | AGCCTCTTACACCCAGTGGAGAA Forward common primer | | | |
| 2 | EAGCTCTCTTGQAGGATCTTGAAGGAA ACTGAATTP E = Threoninol-Hex, Q = BHQ-2, P = phosphate Common detection probe | | | |
| 3 | CCAGACCATGAGAGGCCCTG Reverse common primer | 33.7 | 30.3 | -3.4 |
| 4 | TGTCGAACGCACCGGAGCT Reverse, non-modified mutant primer introduced T:G mm near 5' terminus | 21.6 | 30.5 | 8.9 |
| 5 | GTGCCGAACGCACCGGA-GCT Reverse, pABSA modified mutant primer pABSA modification between the 3rd and 4th nucleotide from 3' terminus | 22 | 32.2 | 10.2 |
| 6 | GTGCCGAACGCACCGGA-GTT Reverse, pABSA modified mutant primer introduced T:G mismatch near 3' terminus pABSA modification between the 3rd and 4th nucleotide from 3' terminus | 24.8 | 42.0 | 17.2 |
| 7 | GTGCCGAACGCACCGGFGC-T Reverse, pABSA modified mutant primer F = tbbdC (also an introduced C:T mismatch) pABSA modification between the 1st and 2nd nucleotide from 3' terminus | 34.9 | 61.5 | 26.6 |

TABLE 1-continued

| SEQ ID NO: | Sequence | MUT Ct | WT Ct | Delta Ct |
|---|---|---|---|---|
| 8 | GTGCCGAACGCACCGGAGC-T Reverse pABSA modified mutant primer pABSA modification between the 1st and 2nd nucleotide from 3' terminus | 22.6 | 36.6 | 14.0 |

Example 2

Primers for Detecting Mutation L858R in the Human EGFR Gene

The amplification reactions shown below were carried out using a detection probe (SEQ ID NO: 10) and forward primer (SEQ ID NO: 9) common to both wild type and mutant targets. The reverse primer in each reaction is: SEQ ID NO: 11, a primer common to both mutant and wild type target. or SEQ ID NO: 12, 13, 14, 15, 16, 17, primers that are matched to the L858R mutant target sequence and mismatched to the wild type target at the 3' terminal base position.

Targets used in these reactions are either pooled human WT genomic DNA (provided by Clontech) or a mutant plasmid construct containing a 500 bp L858R sequence insert into a pUC19 plasmid vector (provided by IDT as a minigene).

Mutant or wild type DNA was amplified in reactions that consisted of 50 mM Tris-HCl (pH 8.0), 80 mM potassium Chloride, 160 μM dATP, 160 μM dCTP, 160 μM dGTP, 320 μM dUTP, 0.1 μM each of selective and common primer, 0.05 μM probe, 200 nM NTQ21-46A aptamer, 40 nM Z05-D Mutant polymerase, 10 units of Z05, and 0.1 mM EDTA, 1.25% DMSO, 2.11% Glycerol, and 2.5 mM magnesium acetate. Mutant or wild type targets were present at starting concentrations of approximately 40,000 copies per reaction.

Amplification and analysis were done using the LightCycler 480 instrument. Reactions were thermal cycled using the following profile: Initial 5 min hold at 50 C followed by 2 cycles of cycles of 95° C. (10-seconds) to 62° C. (30-seconds) and 80 cycles of 93 (10-seconds) to 62 (30-seconds). Fluorescence data was collected at the start of each 62° C. anneal step during the 80 cycle PCR.

It was demonstrated that the pABSA modified primers, SEQ ID NO: 13, 14, 15, 16, 17, are more discriminating than the non-pABSA modified primer (SEQ ID NO: 12). Furthermore, primers that contain both N⁴-ethyl-cytosine and pABSA (SEQ ID NO:13, 14) showed the greatest discrimination. Discrimination is measured as a function of delta Ct between amplification of mutant versus wild type target of equal input (40,000 c). A greater delta Ct is interpreted as greater discrimination between mutant and wild type alleles.

TABLE 2

| SEQ ID NO: | Sequence | MUT Ct | WT Ct | Delta Ct |
|---|---|---|---|---|
| 9 | GTCTTCTCTGTTTCAGGGCATGAAC Common forward primer | | | |
| 10 | FTACTGGTGAAQAACACCGCAGCATG TP Common, detection probe F = threoninol Fam, Q = BHQ-2, P = phosphate | | | |

TABLE 2-continued

| SEQ ID NO: | Sequence | MUT Ct | WT Ct | Delta Ct |
|---|---|---|---|---|
| 11 | CTGGTCCCTGGTGTCAGGAAAA Reverse, common primer | 22.9 | 23 | 0.1 |
| 12 | GCGCCCAGCAGTTTGGCCC Reverse, mutant primer With introduced G:T mismatch near 5' terminus | 22.2 | 26.3 | 4.1 |
| 13 | GCACCCAGCAGTTTG-GJAC pABSA modification between 4$^{th}$ and 5$^{th}$ nucleotide from 3' terminus J = N4-Ethyl-dC, introduced AG mismatch near 3' terminus | 28.7 | 41 | 12.3 |
| 14 | GCACCCAGCAGTTTGGJA-C pABSA modification between 1$^{st}$ and 2$^{nd}$ base, J = N4-Ethyl-dC, introduced AG mismatch near 3' terminus | 32.7 | 41.5 | 8.8 |
| 15 | GCACCCAGCAGTTTGG-CCC pABSA modification between 3$^{rd}$ and 4$^{th}$ nucleotide from 3' terminus, | 22.7 | 28.5 | 5.8 |
| 16 | GCACCCAGCAGTTTGGC-CC pABSA modification between 2$^{nd}$ and 3$^{rd}$ nucleotide from 3' terminus | 22.8 | 30.5 | 7.7 |
| 17 | GCACCCAGCAGTTTGGCC-C pABSA modification between 1$^{st}$ and 2$^{nd}$ nucleotide from 3' terminus | 23.8 | 34.6 | 10.8 |

Example 3

Primers for Detecting Mutation T790M in the Human EGFR Gene

The amplification reactions shown below were carried out using a detection probe (SEQ ID NO:19) and forward primer (SEQ ID NO: 18) common to both wild type and mutant targets. The reverse primer in each reaction is: SEQ ID NO: 20, a primer common to both mutant and wild type target or SEQ ID NO: 21, 22, 23, 24, 25, primers that are matched to the T790M mutant target sequence and mismatched to the wild type target at the 3' terminal base position.

Targets used in these reactions are either pooled human WT genomic DNA (provided by Clontech) or a mutant plasmid construct containing a 500 bp T790M sequence insert into a pUC19 plasmid vector (provided by IDT as a minigen).

Mutant or wild type DNA was amplified in reactions that consisted of 50 mM Tris-HCl (pH 8.0), 80 mM potassium Chloride, 160 µM dATP, 160 µM dCTP, 160 µM dGTP, 320 µM dUTP, 0.1 µM each of selective and common primer, 0.041M probe, 200 nM NTQ21-46A aptamer, 40 nM Z05-D Mutant polymerase, 10 units of Z05, and 0.1 mM EDTA, 1.25% DMSO, 2.11% Glycerol, and 2.5 mM magnesium acetate. Mutant or wild type targets were present at starting concentrations of approximately 40,000 copies per reaction.

Amplification and analysis were done using the LightCycler 480 instrument. Reactions were thermal cycled using the following profile: Initial 5 min hold at 50 C followed by 2 cycles of cycles of 95° C. (10-seconds) to 62° C. (30-seconds) and 80 cycles of 93 (10-seconds) to 62 (30-seconds). Fluorescence data was collected at the start of each 62° C. anneal step during the 80 cycle PCR.

It was demonstrated that the pABSA modified primers, SEQ ID NO: 22, 23, 24, 25, are more discriminating than the non-pABSA modified primer (SEQ ID NO: 21). Furthermore, the primer that contained both tbbdC and pABSA (SEQ ID NO:22) showed the greatest discrimination. Discrimination is measured as a function of delta Ct between amplification of mutant versus wild type target of equal input (40,000 c). A greater delta Ct is interpreted as greater discrimination between mutant and wild type alleles.

TABLE 3

| Seq No. | Sequence | MUT Ct | WT Ct | Delta Ct |
|---|---|---|---|---|
| 18 | CCTCCCTCCAGGAAGCCTACGTGA Common forward primer | | | |
| 19 | JTGCACGGTGGAGGTQGAGGCAGP Common detection probe J = Ja-270, Q = BHQ-2, P = phosphate | | | |
| 20 | TGCGATCTGCACACACCAGTTGA Common reverse primer | 24.12 | 25.99 | 1.87 |
| 21 | CAGTCGAAGGGCATGAGCTGCA Reverse, mutant primer Introduced T:G mismatch near 5' terminus | 23.5 | 30.75 | 7.25 |
| 22 | CAGCCGAAGGGCATGAGC-TGEA pABSA modification between 4$^{th}$ and 5$^{th}$ nucleotide from 3' terminus E = tbbdC | 30.36 | 51.1 | 20.74 |
| 23 | CAGCCGAAGGGCATGAGC-TGCA pABSA modification between 4$^{th}$ and 5$^{th}$ nucleotide from 3' terminus | 24.62 | 34.98 | 10.36 |
| 24 | CAGCCGAAGGGCATGAGCTGC-A pABSA modification between 1$^{st}$ and 2$^{nd}$ nucleotide from 3' terminus | 26.14 | 41.39 | 15.25 |
| 25 | CAGCCGAAGGGCATGAGCGGC-A pABSA modification between 1$^{st}$ and 2$^{nd}$ nucleotide from 3' terminus introduced G:A mismatch near 3' terminus | 29.23 | 45.65 | 16.42 |

The invention claimed is:

1. A method of allele-specific amplification of a variant of a target sequence, the target existing in the form of several variant sequences, the method comprising:
(a) hybridizing a first oligonucleotide and a second oligonucleotide to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein said second oligonucleotide comprises a modified phosphate having a structure:

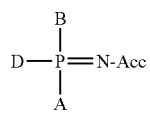

wherein A and B represents a nucleotide chain, D is OH or $CH_3$, and Acc is an electron acceptor or an electron acceptor substituted with a residue R wherein R is an organic substituent, wherein Acc is selected from the group consisting of CN, $SO_2$—R', in which R' comprises at least one amino-substituted alkyl, an optionally substituted aryl or an optionally substituted heterocycle, and a six membered $N^+$ heterocycle with at least one alkylated N-atom in ortho- or para-position, said heterocycle selected from the group consisting of pyridinium, pyrimidinium, and quinolinium;
(b) providing conditions suitable for oligonucleotide extension by a nucleic acid polymerase;
(c) extending said first oligonucleotide and said second oligonucleotide by said nucleic acid polymerase, wherein said nucleic acid polymerase is capable of extending said second oligonucleotide efficiently when said oligonucleotide is hybridized to a variant of the target sequence which is complementary to said at least one selective nucleotide, and substantially less efficiently when said second oligonucleotide is hybridized to a variant of the target sequence which is not complementary to said at least one selective nucleotide;
wherein said second oligonucleotide further comprises a nucleotide with a base covalently modified at the exocyclic amino group, and exhibits discrimination between extension when hybridized to a variant of the target sequence which is complementary to said at least one selective nucleotide and extension when hybridized to a variant of the target sequence which is not complementary to said at least one selective nucleotide that is greater than said discrimination exhibited by said second oligonucleotide either having only said modified phosphate or having only said nucleotide with a base covalently modified at the exocyclic amino group.

2. A method of detecting a variant of a target sequence, the target existing in the form of several variant sequences, the method comprising:
(a) hybridizing a first oligonucleotide and a second oligonucleotide to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein said second oligonucleotide comprises a modified phosphate having a structure:

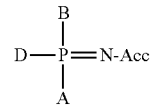

wherein A and B represents a nucleotide chain, D is OH or $CH_3$, and Acc is an electron acceptor or an electron acceptor substituted with a residue R wherein R is an organic substituent, wherein Acc is selected from the group consisting of CN, $SO_2$—R', in which R' comprises at least one amino-substituted alkyl, an optionally substituted aryl or an optionally substituted heterocycle, and a six membered $N^+$ heterocycle with at least one alkylated N-atom in ortho- or para-position, said heterocycle selected from the group consisting of pyridinium, pyrimidinium, and quinolinium;
(b) providing conditions suitable for oligonucleotide extension by a nucleic acid polymerase;
(c) extending said first oligonucleotide and said second oligonucleotide by said nucleic acid polymerase, wherein said nucleic acid polymerase is capable of extending said second oligonucleotide efficiently when said oligonucleotide is hybridized to a variant of the target sequence which is complementary to said at least one selective nucleotide, and substantially less efficiently when said second oligonucleotide is hybridized to a variant of the target sequence which is not complementary to said at least one selective nucleotide;
(d) detecting products of said oligonucleotide extension, wherein said extension signifies the presence of the variant of said target sequence to which said second oligonucleotide has a complementary selective nucleotide;
wherein said second oligonucleotide further comprises a nucleotide with a base covalently modified at the exocyclic amino group, and exhibits discrimination between extension when hybridized to a variant of the target sequence which is complementary to said at least one selective nucleotide and extension when hybridized to a variant of the target sequence which is not complementary to said at least one selective nucleotide that is greater than said discrimination exhibited by said second oligonucleotide either having only said modified phosphate or having only said nucleotide with a base covalently modified at the exocyclic amino group.

3. The method of claim 1, wherein said nucleotide with said base covalently modified at the exocyclic amino group occurs at positions -5, -4, -3, -2 or -1 relative to the 3'-terminal nucleotide.

4. The method of claim 3, wherein said base covalently modified at the exocyclic amino group is selected from a group consisting of N6-benzyl-adenine, N6-para-tert-butyl-benzyl adenine, N4-para-tert-butyl-benzyl cytosine, N4-ethyl-cytosine, and N4-benzyl-cytosine.

5. The method of claim 1, wherein said variant of the target sequence is a mutation of the human EGFR gene.

6. The method of claim 5 wherein said second oligonucleotide is selected from a group consisting of SEQ ID NO: 7, 13, 14, 22.

\* \* \* \* \*